(12) United States Patent
Gedig

(10) Patent No.: US 6,879,401 B2
(45) Date of Patent: Apr. 12, 2005

(54) DEVICE AND METHOD FOR THE EXAMINATION OF THIN LAYERS

(76) Inventor: Erk Gedig, 48153, Muenster (DE)

(*) Notice: Subject to any disclaimer, the term of this patent is extended or adjusted under 35 U.S.C. 154(b) by 0 days.

(21) Appl. No.: 10/324,104

(22) Filed: Dec. 20, 2002

(65) Prior Publication Data

US 2003/0179379 A1 Sep. 25, 2003

(30) Foreign Application Priority Data

Dec. 21, 2001 (DE) .......................................... 101 63 657

(51) Int. Cl.⁷ .............................................. G01N 21/55

(52) U.S. Cl. ....................................................... 356/445

(58) Field of Search ................................. 356/445–448

(56) References Cited

U.S. PATENT DOCUMENTS 6,493,097 B1 * 12/2002 Ivarsson ..................... 356/630

* cited by examiner

Primary Examiner—Gregory J. Toatley, Jr.
Assistant Examiner—Amanda Merlino
(74) Attorney, Agent, or Firm—Bacon & Thomas (57) ABSTRACT

Device for the measurement of thickness changes as well as changes of the physicochemical characteristics of thin layers. The system consists of a preferably monochromatic source of light, a scanning mirror, a preferably on one side metallized prism and a photodetector array. The thin layer is irradiated with light at different angles through the prism by means of the scanning mirror. The reflected image of the layer shows with certain incidence angles when choosing a suitable wavelength, polarization and if needed the metal and the film thickness, resonance-caused intensity fluctuations, by which the layer thickness and refractive index can be calculated.

30 Claims, 6 Drawing Sheets

DEVICE AND METHOD FOR THE EXAMINATION OF THIN LAYERS

FIELD OF THE INVENTION

The invention relates to a device for the spatially resolved measurement of changes of physicochemical characteristics of thin layers applied onto, preferably metal-coated, transparent carriers.

The measurement is done by means of an expanded laser beam, which is directed through the transparent layer and onto the metal film at different angles. When using certain angles and a metal film of suitable thickness, surface plasmons will be excited which interact with the incident electromagnetic field, partially extinguishing the reflected radiation.

The angle of incidence at which the reflection-minimum—the so-called SPR minimum—occurs, is dependent on the index of reflection of the medium adjacent to the metal film.

Highly sensitive real time detection of adsorption- and desorption processes which change the reflection indices are thus possible.

BACKGROUND OF THE INVENTION

The importance of sensor based bioanalytical methods and instruments has been increasing the last couple of years in the sectors of biotechnology and medical research as well as in pharmacological research. The main reason lying in the increasing demand of fast analytical methods that yield quantitative data on biomolecular interactions.

Optical affinity sensors deal with these demands in an ideal way, as they are able to detect without delay, in real time, biomolecular binding events without the utilization of interfering labels.

The arising of highly parallel batches for the analysis of complex nucleic acid- or protein-mixtures, as well as the rising use of combinatorial synthesis procedures within the pharmaceutical active substance search, make the high throughput compatibility of following methods of analysis a central criterion. This need could be favorably covered by optical sensors, which can measure many bonding reactions in parallel. In contrast to the devices available today, such sensors would have to be able to analyze the entire image of a sensor array instead of only a few individual measuring points.

Several different state of the art optical detection principles are well-known which can be used for the real time analysis by biomolecular interactions.

Most procedures use the changes of refractive indices due to binding reactions with the sensor surface.

Most common probably the already explained surface plasmon resonance—SPR sensors, which can be implemented apparatively relatively easily.

The shift of the SPR minimum is normally measured spectrally or, more commonly, angularly resolved.

The spectrally resolved detection, which normally is not as sensitive as the angularly resolved one, is advantageously used in cases in which an angularly resolved detection is not apparatively applicable.

One example is the fiber optic SPR (WO 94/16312 A1), in which light from a broadband source is coupled into a gold-coated optical fiber and the shift of the resonance wavelength is measured.

The angularly resolved detection is described, for example, in WO 90/05305. In this apparatus, a metal film is illuminated with convergent light beams, and the angle shift is observed by means of a diode array/lens system-combination.

Such a device demands a relatively large, mechanically very massive measuring head, which makes such an apparatus lavish. A apparativly simpler variant, as described in DE 19817472, only uses two photodiodes to determine the SPR minimum shift, making this apparatus a little bit simpler.

A principally different principle is described by Kooyman et al. (R. P. H. Kooyman, A. T. M. Lenferink, R. G. Eenink and J. Greve (1990) Anal. Chem. one, 63, pp. 83–85). Here the angle of the incident laser beam is varied over time with a scanner mirror and the corresponding change of intensity of the reflected light is detected by means of a photoelectric cell. The system described there supplies good results when measuring few points and is relatively unelaborate.

Other detection principles comprise, for example, the Resonant Mirror (Cush, R., Cronin, J. M., Goddard, N. J., Maule, C. H., Molloy, J. und Stewart, W. J. (1993) *Biosensors & Bioelectronics,* 8, pp. 347–353), the integrated optical interferometer (DE 4033357), the difference-interferometer (Fattinger, Ch., Koller, H., Schlatter, D. und Wehrli, P. (1993) *Biosensors & Bioelectronics,* 8, pp. 99–107), the grating coupler (Tiefenthaler, K. (1992) Advances in Biosensors, Vol. 2, pp. 261–289) or the Reflectometric Interference Spectrometer (DE 19615366 A1).

The production of the exchangeable sensor is clearly more complex in all these enumerated techniques than with the SPR, this being one of the reasons, besides others, for them being inferior to the SUPERCHARGER.

All procedures specified above have in common that they do not work spatially resolved and thus cannot cope with multiple analytes.

In past years several methods were therefore developed, which make parallel measuring possible on different parts of the sensor chip.

In this regard, a further development of the above already mentioned grating coupler is described, e.g., in WO 95/03538 or EP 1031828 A1; a spatially resolved reflectometric interference spectrometer is known from DE 19828547 A1.

Apart from the disadvantage of the complex manufacturing of the exchangeable sensors, these systems also have the disadvantage that they divide the sensor surface into discrete and relatively large parts and the devices therefore become either quite large or exhibit a limited capacity.

As the SPR sensors are technically easier to implement and theoretically allow a nearly arbitrarily small partitioning of the sensor surface, clearly more implementation solutions exist. The first picture-giving SPM (Surface Plasmon Microscope) was developed in 1988 (Knoll, W. and Rothenhaeusler, B. (1988) Nature, 332, pp. 615–617).

In this and other well-known procedure (DE 19829086, as well as Frutos, A. G. and Corn, R. M. (1998) Anal. Chem., July 1, pp 449A–455 A) a widened laser beam is radiated on a metal surface at a fixed angle and the changes of intensity of the picture reflected on a CCD camera is evaluated. The main disadvantage of this method is that only intensity changes of the pixels are recorded and not the angles of the SPR minima.

This results in a clearly worse sensitivity and a strongly reduced dynamic range. In addition, some changes of individual brightness values might be ambiguous under some conditions—it then cannot be determined in which direction the SPR minimum is shifted.

An improvement of the described SPM technology is revealed in DE 3909144. A picture of the sensor surface is recorded using different incidence angles and the SPR minimum angles for up to 5×5 µm small surface sections are determined with downstream image processing. Although quite a high accuracy can be obtained with this procedure in principle, incidence and reflection angles must both be changed for imaging, which is mechanically complex and which can only be realized using a low data acquisition frequency. A two-dimensional fast real time analysis of bonding reactions on the chip surface is therefore not possible with this arrangement.

A spatially resolved SPR sensor with spectral detection is well-known from WO 00/22419. However, it uses mobile hole or slit apertures, in order to successively light up different ranges of the sensor surface, increasing the mechanical complexity, slowing down the data acquisition frequency and setting the size of the individual measuring points to a fixed value from the beginning on.

An angularly resolved SPR equipment with spectral detection is described in WO 99/30135. For the utilization as imaging sensor the use of a mask or a lens array is suggested. The disadvantages of this arrangement closely correspond to those of the sensor mentioned in the preceding section.

A system with mechanical change of the incidence angle and likewise mechanical change of the XY position of the measuring point on the sensor chip is known from WO 00/46589. Unfavorable are, above all, the complex structure and large mobile mechanical components, which entail a low data acquisition frequency.

Moreover, EP 0973023 describes a compact SPR transducer with angle resolved detection. The measuring range and the detector array are here divided into several areas, for which separate SPR signals are recorded. The areas of the individual sensitive regions are determined by the size of the transducers and are thus relatively large. A real high throughput ability might therefore only limits the application as a biosensor.

WO 98/34098 describes a spatially resolved SPR sensor with a complex lens and mirror system for the synchronously detection of the SPR minimum angles for a multiplicity of pixels. A relatively high measuring frequency can be realized using this scheme, but it also is a very complex contraption.

SUMMARY OF THE INVENTION

In summary it can be said that a high resolution SPR transducer with a fast measuring of the SPR minimum angle for each pixel has only been developed in very complex contraptions until today. It is thus the object of the given invention to make available such easily implementable equipment.

This object is achieved by the device for the optical examination of thin layers, comprising a carrier with a surface; a device for the illumination of the surface of the carrier with parallel aligned light under different angles of incidence; a detector for the spatially resolved detection of the intensity of the radiation for different angles of incidence, reflected by the surface of the carrier; and an analysis unit, for the spatially resolved determination of the dependence of the intensity of the reflected light on the incidence angle, on the basis of the spatially resolved acquisition of intensities for different angles of incidence, whereby the detector for acquisition of the reflected radiation does not have to be adjusted for the different angles of incidence of the reflected radiation.

The device for illuminating the surface of the carrier with parallel light comprises preferably a monochromatic light source, such as an LED or a laser. To avoid, respectively to minimize intensity fluctuations, stabilised or controlled lasers and controlled diode lasers or He—Ne lasers in particular are advantageous. Preferably, the intensity fluctuation of the light source should not exceed 0.4% and more preferred not exceed 0.2%. With the preferred stabilized light source, a RMS noise of less than $0.7*10^{-3\circ}$ can be achieved; with the more preferred stabilisation, the RMS noise of the resonance angle can be reduced to values below $0.3*10^{-3\circ}$.

The carrier comprises for the coupling of the incidence light, for example, a triangular or trapezoidal prism or a plate with individual prisms, whereby the basis of the prism and/or the prisms is either the carrier top side or the surface, respectively, by which the incidence light is reflected, or serves as surface on which a preferably in optical regard flat-parallel plate is put on. In this case reflection takes place from the surface of this flat-parallel plate, which then forms the carrier top side.

The carrier top side is coated with a metal film in devices for the execution of surface plasmon resonance spectroscopy which helps to create a plasmon resonance minimum as sharp as possible. Ag or Au films are particularly suitable, whereby their thickness preferably amounts to about 45 to 55 nm.

In a further setup the gold layer is on a lattice or on a multiplicity of parallel arranged small prisms, respectively. This arrangement has the advantage that it can be realized economically by injection moulding in plastic and the carriers and the prism form a unit, which can be easily replaced.

The detector of the device according to the invention is suitable to detect the reflected radiation of a section of the surface of the carrier over a sufficiently large angle range. The angle range amounts preferably to at least ±1.5° around a mean angle, whereby the mean angle can particularly equal for instance the resonance angle of the plasmon resonance.

The mean angle is adjustable in the embodiment preferred at present, in order to adapt the position of the detector to individual experimental conditions. During the operation of the device according to the invention, i.e. during the spatially resolved acquisition of the radiation reflected by the carrier, the detector however does not any longer need to be adjusted to the changed angle, since the detector surface is laid out sufficiently large to acquire the reflected radiation over the entire angle range.

The device according to the invention thus makes a fast acquisition of the reflected intensity possible for different angles, since a mechanical adjustment of the detector does not have to be made, and thus acceleration forces arising with such movements do not have to be taken under consideration. Furthermore, this leads to a simplified mechanical and optical contraption, which substantially reduces the manufacturing costs of the device according to the invention.

The angle range around a mean angle, detectable by the detector, further preferentially amounts to at least ±2.5°, and particularly preferentially at least ±5°. The acquirable angle range around a mean angle is favorably not larger than ±20°, further preferentially not larger than ±15°, and particularly preferentially not larger than ±10°.

The detector for the spatially resolved acquisition of the intensity of the radiation reflected by the carrier top side, is preferably a photodiode array or a CCD camera. Especially preferred are CMOS cameras which allow for a higher image aquisition frequency.

In addition, the device according to the invention is preferably outfitted as a surface plasmon resonance spectrometer, although other methods of detection, such as brewster angle microscopy and ellipsometry, can be used in principle.

The dependence of the intensity of the reflected light on the angle of incidence can be seized spatially resolved with the device according to invention, whereby same points of the illuminated surface of the carrier or the carrier top side, respectively, are projected onto different points of the detector during the change of the incidence angle.

The angle of incidence is varied by means of a rotating mirror or a scanning mirror, respectively, in the arrangement preferred at present. In this arrangement identical parts of the incidence parallel beam fall onto different points of the surface of the carrier or carrier top side, respectively, due to the change of the incidence angle.

The scanner mirror is preferably a galvoscanner, whose control voltage is sufficient to determine the current incidence angle. In another arrangement of the invention, one part of the light beam reflected by the mirror is reflected directly onto a second detector, whereby the angles of incidence can be determined from the position of this part of the light beam on the second detector. In a further alternative an angle sensor is attached to the axle of the scanning mirror, which directly gives an angle dependent signal. Instead of a scanning mirror which oscillates around a medium angle, a monotonously rotating polygon mirror can be employed as well.

The analysis unit can be, e.g., a computer, preferably with a data storage capability for storing the information on the spatially resolved distribution of the intensity of the light reflected by the surface for different angles; and a data processing unit, which determines, on the basis of the spatially resolved intensity distributions measured using different incident angles, the intensity for different points on the surface of the carrier as a function of the incidence angle. Then at least one characteristic of the layer prepared on the carrier can be determined using angle dependent intensities for different points of the surface by this or another data processing unit. This can be in particular the characteristic layer thickness or the dielectric characteristics of the layer. Details for the determination of the layer thickness or the dielectric characteristics of a layer, respectively, on the basis of the angle dependent distribution of intensity are known to, for example, the specialist in the field of the surface plasmon resonance spectroscopy and do not need to be discussed in detail here.

The device according to the invention is preferably suitable for the described spatially resolved angle dependent intensity measurement and the determination of at least one layer characteristic in a continuous mode, i.e., the angle dependent intensity measurement over the angle range of interest and the following evaluation is done repeatedly.

The angle of incidence is preferentially controlled by the computer of the evaluation unit. The angle range which should be covered is preferably variably adjustable, in order to adapt to the respective experimental task.

Also, the increment between the individual angles, with which a measurement of the intensity takes place, is variable in the preferential set-up. It is intended in a further set-up that the incrementation steps are not equidistant, but can be adapted according to the information content of the individual angle ranges, i.e. the incrementation around the minimum of the plasmon resonance can be chosen smaller than in angle ranges lying outside of the resonance.

In another embodiment the automatic determination of the incrementation is further possible. In an initialization mode the intensity curve is hereby first roughly determined, and on the basis of the determined curve the increment is specified for the individual angle ranges and/or the entire angle range is reduced to a relevant range, for example the determined plasmon resonance angle $\pm 1.25°$ or $\pm 2.5°$ or $\pm 5°$, respectively. With many applications the expected position of the resonance angle is known and it is then possible to skip the above described initialization mode. As an example, the angle range which is scanned could be $\pm 2.5\%$ around the expected resonance angle.

The data analysis of the light reflected from the sample requires as first step a correction of the image shift, i.e. as with changing scan angle the image of the sample moves over the sensitive area of the camera, each spot on the sample surface has to be ascribed to the corresponding pixels at this angle. In principle this shift can be mathematically calculated and corrected. When lenses are used between sample and light source and/or detector respectively, in the fringe areas distortions of the measured image might occur which are analytically hard to describe. In such cases an experimental determination of the image shift is preferred. Such experimental correction can be achieved for example by projecting onto the camera a sufficiently fine grid which lies on top of the carrier instead of the sample. The well defined positions of the grid are then recorded for each different angle. The thus created angle/pixel matrix allows to unambigously ascribe pixels to sample areas at different angles of incidence. Should it be feasible to describe the image shift between two given angles precise enough by interpolation between these two angles, it is sufficient to store the shifts of these two angles and calculate the data of the remaining angles by interpolation.

Generally, two modes of interaction between detector and data processing unit are possible:

In the first variant the camera processes for each scanned angle all image data to the following data processing unit. This mode produces huge data quantities and is therefore slow.

Other variants include a certain degree of data pre-processing already in the camera. Such pre-processing can for example be achieved by bundling the pixels of certain regions of interests (ROIs). For these ROIs only the average, the minimum and the maximum intensity are processed. In this case the quantity of transferred data is much lower and the data processing speed thus significantly increased.

The aforementioned reduction of data analysis and processing to defined ROIs can be insofar advantageous as the image of the sample contains frequently large areas which do not contribute to the information content of the sample. Such areas are for example the regions between the spots of a microarray.

Insofar as the pixel positions of the ROIs are known for defined angles, for example according to the above described method, the readout of the detector and the image analysis can be reduced to only these pixels which, under angles close to resonance, receive light from the ROIs. Especially CMOS cameras are well suited for such mode of operation.

The procedure or method according to the invention for the analysis of thin layers, is essentially a procedure, in which the layers are illuminated under different incidence angles with parallel light beams in ways so that the light is reflected onto a two-dimensional detector, and with which the layer thickness or another layer characteristic is then computed spatially resolved on the basis of the angle dependent differences in intensities of the reflected light; characterised by the fact that image distortions, due to the change of angle and a detector that does not adapt to these changes of angle, are corrected before determining any layer characteristics. The correction in particular takes place via electronic data processing. Before the determination of the layer characteristics preferentially a correction of the brightness fluctuations, that do not have their source in properties of the sample to be examined, is applied.

This can be, for example, a correction needed due to different intensities of the different parts of the light beam of the incidence light, and/or a correction for the angle dependent transmission function of the entire optical arrangement and/or a correction for local inhomogeneities of the detector for the spatially resolved acquisition of the angle dependent distribution of intensities of the reflected light.

The invention also covers a computer program for the controlling of a device for the execution of the procedure according to the invention.

Further advantages and criteria result from the claims, the description and the designs.

DETAILED DESCRIPTION OF THE DRAWINGS

DESCRIPTION OF THE PREFERRED EMBODIMENTS

Figure 1:
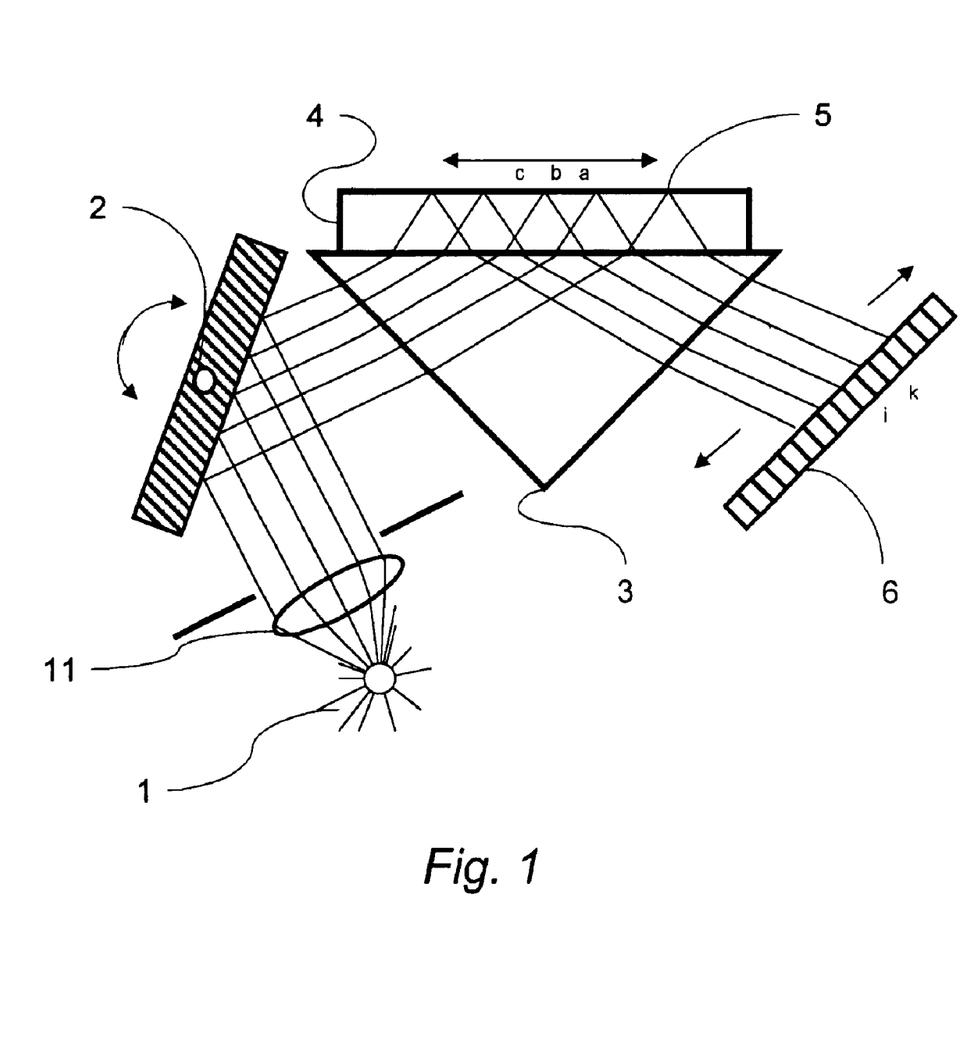
FIG. 1 shows a schematic view of a device according to invention.

The invention is to be described in more detail hereafter on the basis of an example shown schematically in FIG. 1. An exemplary optical design of a surface plasmon resonance sensor, or SPR sensor, according to the invention, as well as a path of beams arising during the measuring process are shown. The optical system consists of a preferably monochromatic source of light 1, preferentially a laser or a laser diode of suitable wavelength, whose radiation is polarized by means of a (not shown) polarization filter parallel to the plane of incidence of the sensor chip 4, which here serves as a substrate for the SPR.

The diameter of the laser beam is first broadened with a commercial beam expander 11 and steered with a scanner mirror 2 under different angles of incidence onto the entrance surface of a prism 3.

A subrange of the broadened beam falls under different angles of incidence onto the underside of a sensor chip 4 residing on the prism 3, which is coated on its top side 5 with a SPR capable gold layer.

The sensor chip 4 is optically connected with the prism 3 by means of immersion oil or a suitable plastic. Optionally, the gold layer can be vapour-deposited directly on the top side of the prism 3, however the sensitive area is then no longer exchangeable.

The illumination of the sensor chip under different angles of incidence is done in such a manner that the parallel light beams move over the surface during the measurement, however completely illuminating it at any time; a certain point a, b, c of the sensor chip is thus lit up by different parts of the light ray bundle depending on the angle of incidence.

In a preferred arrangement the incidence angle is scanned with a light wave of the length of 660 nm within a range of ±5° around a mean angle of about 75°.

The light reflected by the gold coated surface 5 leaves the prism and falls on an image processing detector 6, preferably a CCD detector or a photodiode array.

Figure 2:
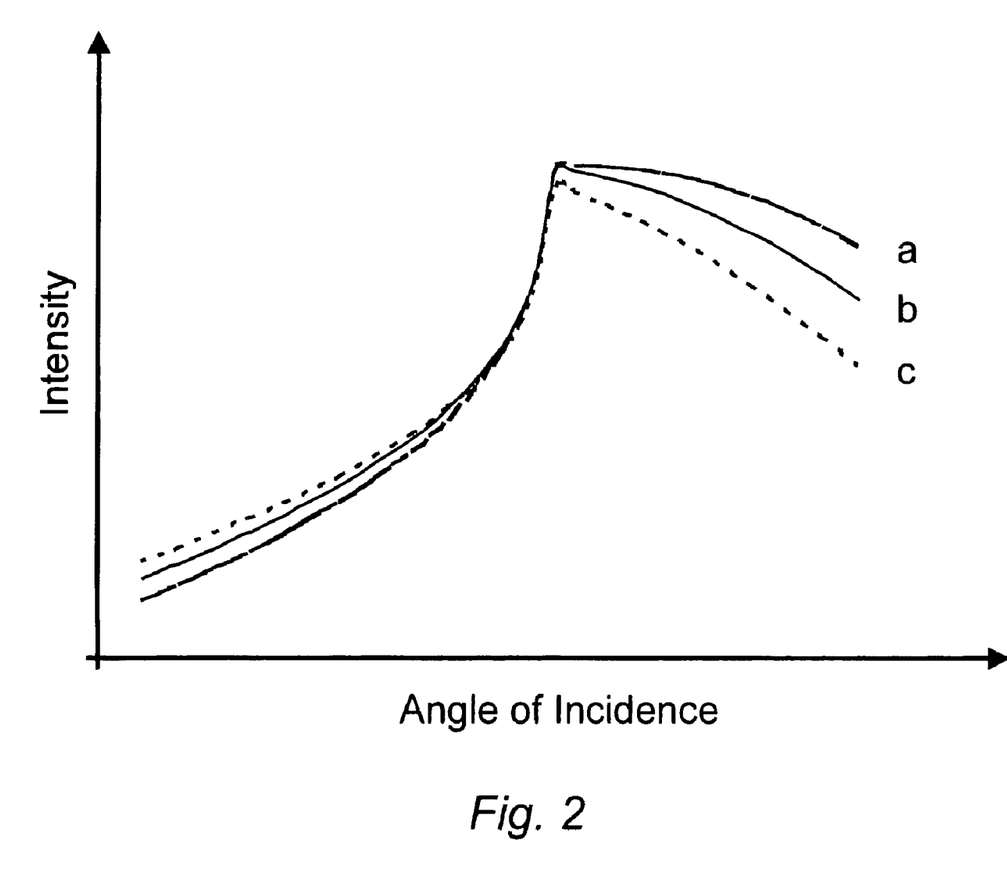
FIG. 2 shows the angle dependence of the intensity of the reflected radiation for different sample positions without any plasmon resonance being present.

FIG. 2 for example shows the effect of the different intensities of the different parts of the incidence light beam on the intensity of the reflected light from the points a, b, c of the surface 5, which reaches the detector 6.

In this case the surface 5 does not exhibit SPR. All curves show the characteristic total reflection edge and otherwise the behavior given by the transmission characteristics of the boundary surfaces. The curves however deviate from each other insofar, that the points a, b, c are illuminated with maximum intensity at different angles.

Figure 3A:
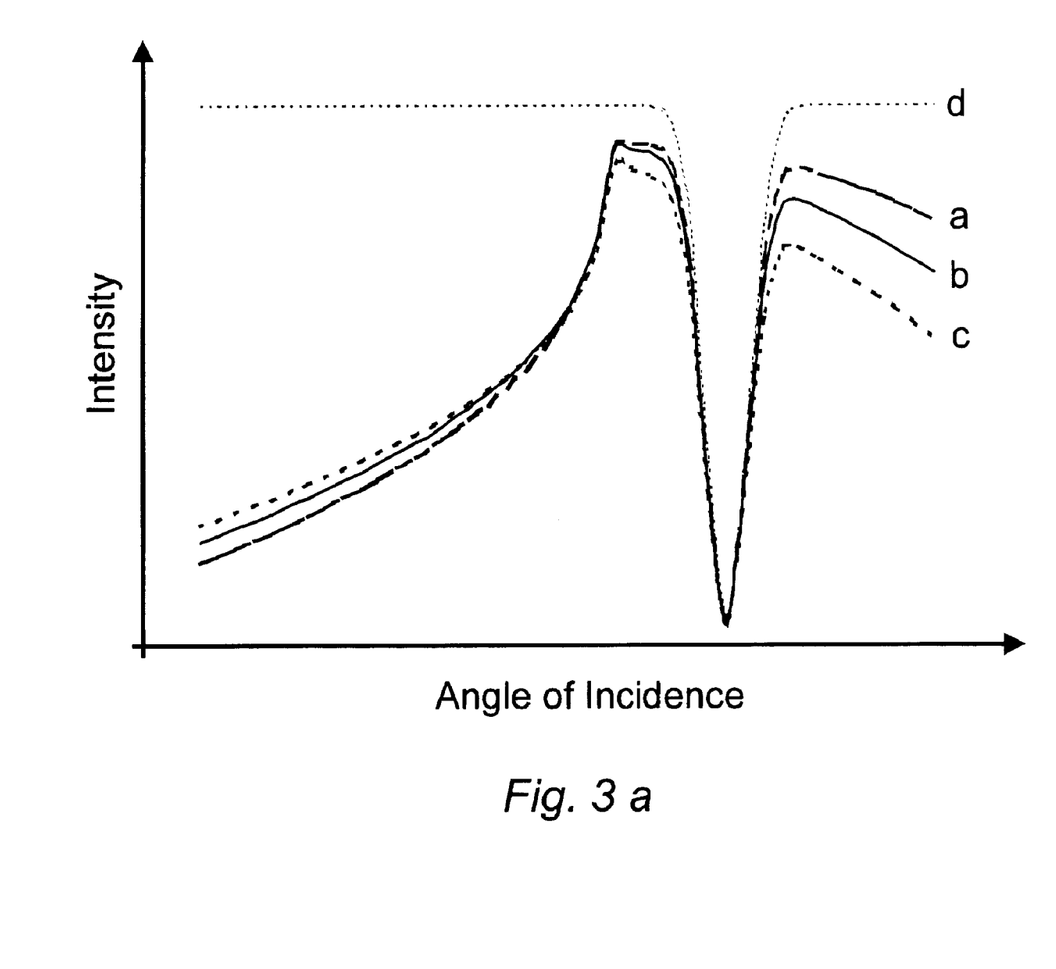
FIG. 3a shows the angle dependence of the intensity of the reflected radiation for different sample positions with plasmon resonance being present.

FIG. 3a shows how the different incidence intensities described before affect the signal of a plasmon resonance received by the detector.

The actual resonance behavior is shown in curve d, whereby the signal received by the detector 6 of the points a, b, c, has the shape marked by the appropriate letters. By normalization with the curves of the FIG. 2 the actual resonance characteristic d for the respective points a, b, d can be found if necessary.

Making it more difficult is the fact that the points a, b, c of the sensor chip 4 are projected onto different areas i, k of the array 6 depending upon the angle of incidence.

Figure 4:
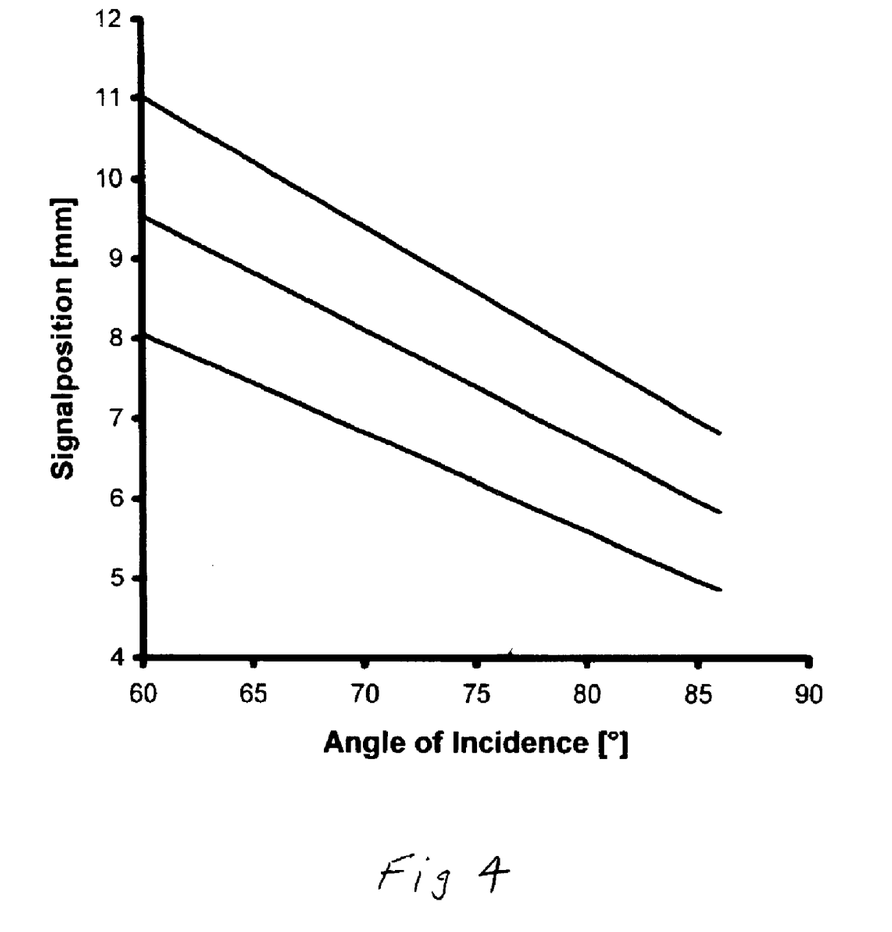
FIG. 4 shows the angle dependence of the signal position on the detector for different positions on the sensor chip.

The angle dependent image shift of the signal of the points a, b, c is represented schematically in FIG. 4. It is therefore necessary to assign by means of an appropriate analysis device and a correction algorithm the individual pixels i, k of the CCD array 6 to certain point a, b, c on the sensor chip surface 5 depending upon the incidence angle (position of the scanner mirror 2). The brightness fluctuations of the reflected partial light beams caused by beam inhomogeneities for example, as discussed above, can be corrected at the same time or sequentially.

Figure 3B:
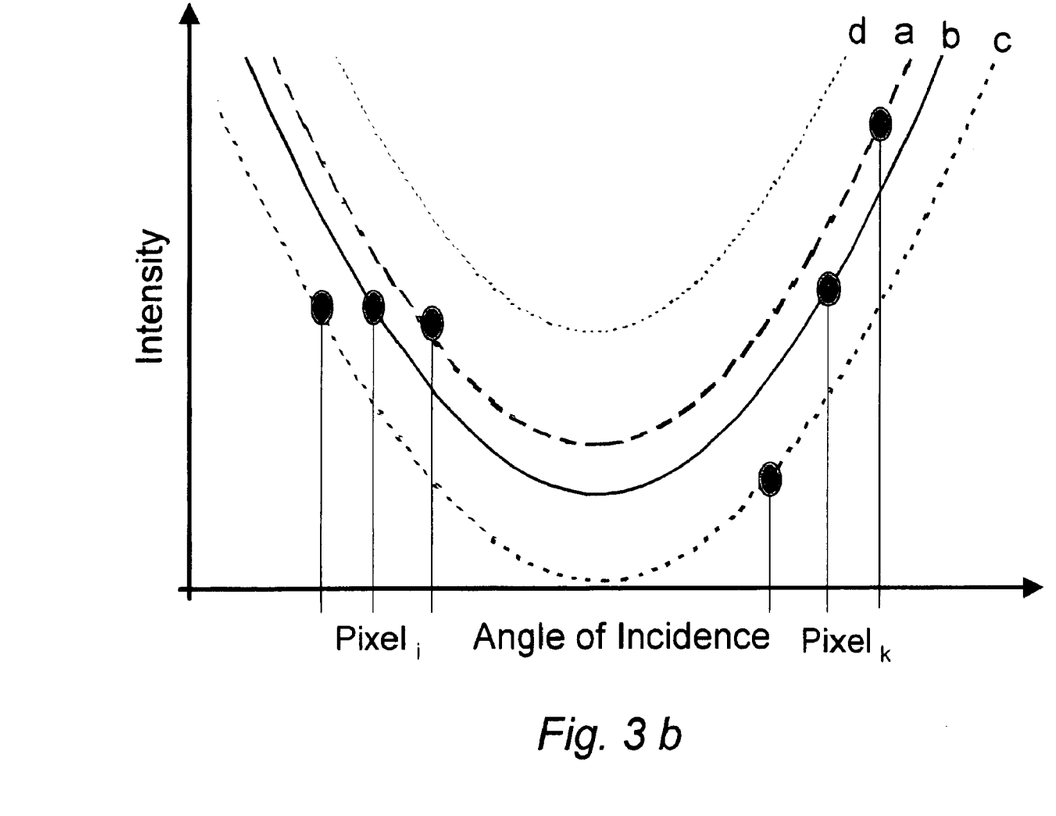
FIG. 3b shows a zoomed display of the resonance minimum of the intensity of the reflected radiation for different sample positions.

The effect of the described image-shift and the intensity inhomogeities for the range around the plasmon resonance angle is shown again in FIG. 3b.

A first pixel i receives reflected light from the resonance minimum first from the point a, then from the point b, and finally from the point c with increasing angle.

Coincidentally, the selected first pixel i for these points has the same intensity with different angles. A second pixel k receives the signals from the points a, b, c after the passage through the resonance minimum. Here a dramatic rise of intensity for the signal of the points a, b, and c is observed. This example shows that it is therefore of highest importance for the success of the described procedure, to assign those signals acquired by a pixel i, k the correct angle and the correct point a, b, c of the chip surface 5.

Figure 5:
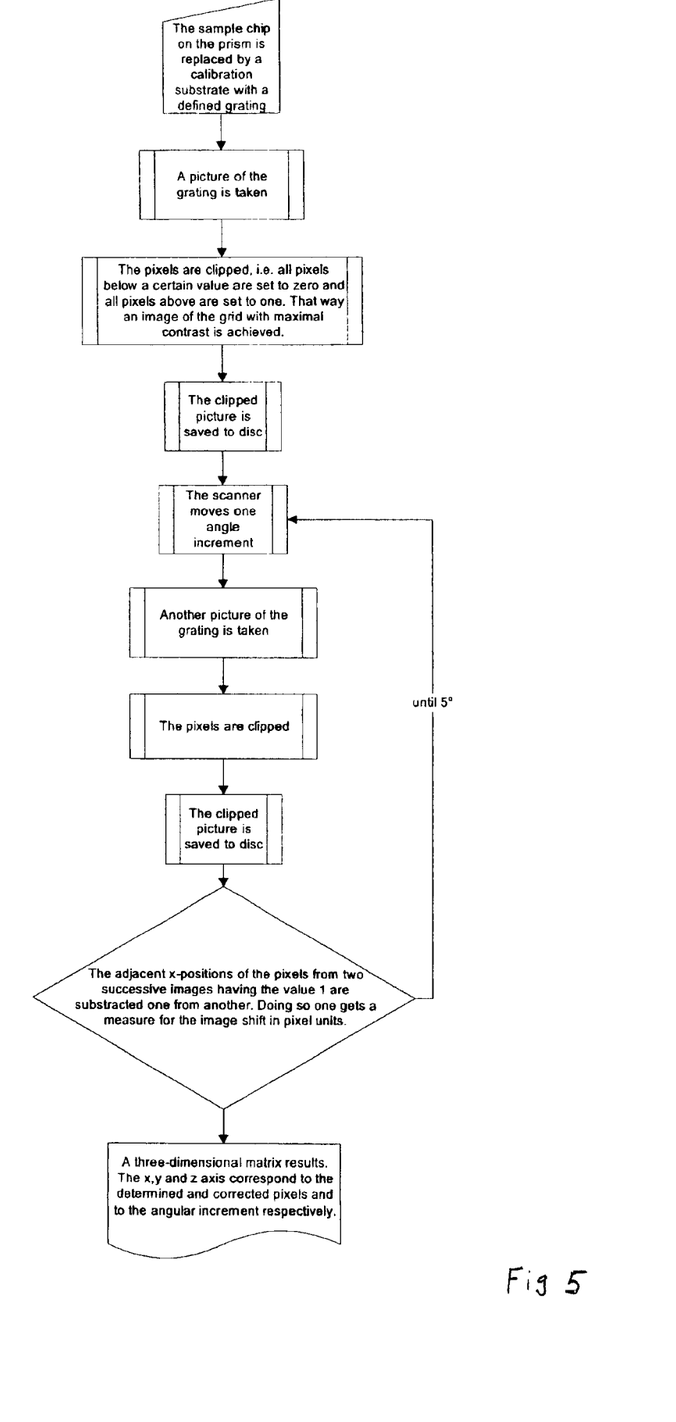
FIG. 5 shows a flow scheme concerning a method for calculating the image shift for different angles of incidence

FIG. 5 shows a flow scheme for a method which can be used for such assignment. According to this method, a coordinate grid with high contrast is inserted instead of a sample. The image of this coordinate grid is then recorded for different angles and the spots of the coordinate image are with the help of a discriminator set either to a bright or to a dark value. Thus the coordinate image can be easily analyzed and an unambigously assignment of the sample areas to pixels for different angles of incidence is possible. The image shift is stored as data matrix for different angles of incidence and can later be used for the correct assignment of the pixels when samples are analyzed.

According to the above principles, the intensity of the reflected signal of individual positions a, b, c on the chip surface 5 can be measured spatially resolved as a function of the respective angle.

A SPR curve measured in such a way can be fitted to simulated curves for the increase of the accuracy with the help of the Fresnel theory (see H. Wolter in 'Handbuch der Physik', ed. S. Flügge, Springer). The incidence angle, at which the intensity of the reflected light becomes a minimum, is the so-called SPR angle.

The position of the scanner mirror 2 in the embodiment preferred at present, needed for the calculation of the SPR angle, is calculated with sufficient accuracy from the control voltage used by the galvoscanner.

Under the condition of good resolution of the used CCD camera and sufficient capacity of the downstream image processing hard- and software, the SPR minimum angle can be determined at the same time for several millions pixels with a frequency of over 10 Hz.

This is sufficient, in order to ensure a fast real time detection of binding reactions at the sensor surface 5. It is possible to do this without complex and expensive optical components because of the electronic correction of image distortions and intensity fluctuations arising during the angle scans.

It is to be mentioned here that, procedures according to the invention described above with SPR, can also be applied with other, related techniques. These are in particular brewster angle spectrometry and ellipsometry. However, the appropriate measurement setups, easily designed by a specialist with appropriate expertise, are contraptions more complex than SPR devices, and are thus not dealt with in greater detail here.

For the measurement of the interaction, respectively the adsorption, of biological or chemical molecules, the optical detector system described above can be combined with a device for application of liquids or gases. This device is put onto the surface 5 of the chip 4. Depending upon the intended purpose, a sample can be brought in contact with the entire surface of the sensor chip 4 or a multiplicity of samples independently of each other in contact with different parts of the sensor chip. It is then possible to examine thousands of different samples within a short time.

With certain applications it is useful to bundle the intensities of a pixel population by so-called binning. This is preferred the case if these pixels detect light which is reflected from a uniform sample area. Binning is especially advantageous when the carrier or the sample chip carry a large number of discrete and homogeneous regions, as it is the case on a spotted biochip. The angle-dependent intensity of the so assigned pixels corresponds to the mean signal of the corresponding discrete sample region. Such averaging can also be done in a weighted manner, such that the peripheral areas of a given sample region contribute more or less to the signal. With applications which require said binning of certain regions, it seems to be feasible to restrict the data aquisition to such pixels which receive light from the relevant sample areas. A selective read-out of pre-defined ROIs is especially possible with CMOS cameras. CCD cameras are less suited for this purpose.

What is claimed is:

1. A device for the optical examination of thin layers, comprising:

a carrier substrate with a surface;

a device for the illumination of the surface of the carrier under different angles with parallel light beams;

a detector for the spatially resolved acquisition of the intensity of radiation reflected by the surface of the carrier for different angles of incidence; and an analysis unit, for the spatially resolved determination of the dependence of the intensity of the reflected light on the incidence angle on the basis of the spatially resolved intensity acquired for different angles of incidence, characterized in that the detector does not have to be moved to follow the shifting reflected radiation for the acquisition of the reflected radiation for different angles of incidence of the reflected radiation, wherein:

same beams of the incident light irradiate different parts of the carrier surface during the scan of the incidence angle.

2. The device according to claim 1, wherein:

the light reflected from any position of the surface of the carrier for different angles of incidence is projected onto a different area on the detector.

3. The device as claimed in claim 1, wherein:

the change of the incidence angle over time is made by means of a movable mirror, preferably a galvoscanner.

4. The device as claimed in claim 3, wherein:

the incident angle which is scanned over time is measured through the voltage applied to the galvoscanner.

5. The device according to claim 1, wherein:

the detector covers a photodiode array or a CCD camera.

6. The device according to claim 1, wherein:

the carrier is transparent.

7. The device according to claim 6, wherein:

the carrier exhibits a layer of metal on the surface.

8. The device as claimed in claim 1, wherein:

the incidence angle of the light irradiated on the carrier is detected before or after the reflection at the carrier top side by means of a second photodetector.

9. The device as claimed claim 1, wherein:

brightness fluctuations arising from shifts of the projection of the carrier on the detector due to the change of the incidence angle and/or not based on changes of the layer characteristics are corrected by means of an image processing software before the determination of the layer characteristics.

10. The device as claimed in claim 6, wherein:

the carrier is made from a transparent plastic.

11. The device as claimed in claim 6, further comprising:

a second transparent carrier, which is optically coupled with the first carrier.

12. The device according to claim 11, wherein:

the second transparent carrier consists of an inorganic dielectric.

13. The device according to claim 12, wherein:

the second transparent carrier is made of glass.

14. The device according to claim 11, wherein:

the first and second transparent carriers consist of plastic.

15. The device according to claim 6, wherein:

the transparent carrier is carried out as a prism.

16. The device according to claim 6, wherein:
the transparent carrier consists of at least two parallel arranged prisms or a prism grating.

17. The device according to claim 6, wherein:
the transparent carrier is exchangeable.

18. The device according to claim 1, wherein:
the incident light is monochromatic and preferably laser light.

19. The device according to claim 1, wherein:
the incident light is polarized.

20. The device according to claim 1, wherein:
several pixels on the detector are bundled and averaged by image analysis software.

21. The device according to claim 7, wherein:
the metallic film is divided into several areas separated from each other.

22. The device according to claim 7, further comprising:
a unit in order to subject the side of the metallic film that is opposite of the transparent carrier with liquids and/or gases.

23. The device according to claim 22, wherein:
the metallic film can be subjected independently with liquids and/or gases at at least two different, preferably a large number, of separate areas.

24. A device for the optical examination of thin layers, comprising:
a carrier substrate with a surface;
a device for the illumination of the surface of the carrier under different angles with parallel light beams;
a detector for the spatially resolved acquisition of the intensity of radiation reflected by the surface of the carrier for different angles of incidence; and
an analysis unit, for the spatially resolved determination of the dependence of the intensity of the reflected light on the incidence angle on the basis of the spatially resolved intensity acquired for different angles of incidence, characterized in that
the detector does not have to be moved to follow the shifting reflected radiation for the acquisition of the reflected radiation for different angles of incidence of the reflected radiation, wherein:
the light reflected from any position of the surface of the carrier for different angles of incidence is projected onto a different area on the detector.

25. The device according to claim 24, wherein:
same beams of the incident light irradiate different parts of the carrier surface during the scan of the incidence angle.

26. A device for the optical examination of thin layers, comprising:
a carrier substrate with a surface;
a device for the illumination of the surface of the carrier under different angles with parallel light beams;
a detector for the spatially resolved acquisition of the intensity of radiation reflected by the surface of the carrier for different angles of incidence; and
an analysis unit, for the spatially resolved determination of the dependence of the intensity of the reflected light on the incidence angle on the basis of the spatially resolved intensity acquired for different angles of incidence, characterized in that
the detector does not have to be moved to follow the shifting reflected radiation for the acquisition of the reflected radiation for different angles of incidence of the reflected radiation, wherein:
the change of the incidence angle over the time is made by means of a single movable mirror, such that the angle-change causes image shifts on the detector, the device further comprising computing means for correcting the image shifts on the detector.

27. A procedure for the investigation of thin layers, comprising the steps of:
irradiating the layers under different incidence angles with parallel oriented light in such a manner that the light is reflected onto a two-dimensional detector; and
changing the incidence angle over time by means of a single movable mirror, such that the angle-change causes image shifts on the detector, wherein:
the image shifts on the detector are corrected by computing means, before the layer characteristics are determined.

28. The procedure according to claim 27, wherein:
brightness fluctuations exclusively due to angle-changes are electronically corrected before the determination of the layer characteristics.

29. The procedure according to claim 27, wherein:
the changes of characteristics of the layers are measured by means of surface plasmon resonance, brewster angle spectrometry or ellipsometry.

30. A data processing program loadable into a computer, in particular on a data storage medium, for controlling a device used for the execution of the procedures claimed in claim 27.

* * * * *